(12) United States Patent
Helle et al.

(10) Patent No.: US 11,199,604 B2
(45) Date of Patent: Dec. 14, 2021

(54) MRI INVOLVING THE ACQUISITION OF AN ANGIOGRAPHY WEIGHTED IMAGE AND OF A PERFUSION WEIGHTED IMAGE

(71) Applicant: KONINKLIJKE PHILIPS N.V., Eindhoven (NL)

(72) Inventors: Michael Gunter Helle, Eindhven (NL); Matthias Johannes Paulus Van Osch, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 1205 days.

(21) Appl. No.: 15/303,758

(22) PCT Filed: Apr. 17, 2015

(86) PCT No.: PCT/EP2015/058359
§ 371 (c)(1),
(2) Date: Oct. 13, 2016

(87) PCT Pub. No.: WO2015/158879
PCT Pub. Date: Oct. 22, 2015

(65) Prior Publication Data
US 2017/0160365 A1 Jun. 8, 2017

(30) Foreign Application Priority Data
Apr. 18, 2014 (EP) .................................... 14165302

(51) Int. Cl.
*G01R 33/563* (2006.01)
*G01R 33/483* (2006.01)
(Continued)

(52) U.S. Cl.
CPC ...... *G01R 33/56366* (2013.01); *A61B 5/0044* (2013.01); *A61B 5/026* (2013.01);
(Continued)

(58) Field of Classification Search
None
See application file for complete search history.

(56) References Cited

U.S. PATENT DOCUMENTS

| 7,047,060 B1* | 5/2006 | Wu ....................... G01R 33/563 324/307 |
| 2009/0088626 A1* | 4/2009 | Sutton .............. G01R 33/56308 600/419 |

(Continued)

OTHER PUBLICATIONS

Wells et al., "In Vivo Hadamard Encoded Continuous Arterial Spin Labeling (H-CASL)", Magnetic Resonance in Medicine, vol. 63, pp. 1111-1118, 2010. (Year: 2010).*

(Continued)

*Primary Examiner* — Katherine L Fernandez

(57) ABSTRACT

The present invention provides a method for magnetic resonance (MR) imaging of a subject of interest (120) using arterial spin labeling, comprising the steps of performing a labeling module (200) by applying magnetic and/or radio frequency (RF) fields to the subject of interest (120) for labeling arterial blood in at least a labeling region (144) thereof, performing a first readout module (202) to obtain first MR information of the subject of interest (120) in a region of interest (142) using first parameters, performing a second readout module (204) to obtain second MR information of the subject of interest (120) in a region of interest (142) using second parameters, and performing MR image generation of a region of interest (142) based on the first and second MR information, wherein the first and second parameters of the first and second readout module (202, 204) are chosen to be different parameters. The invention also provides a MR imaging system (110) adapted to perform the above method and a software package for upgrading a MR imaging system (110), whereby the software package con- (Continued)

tains instructions for controlling the MR imaging system (110) according to the above method.

20 Claims, 6 Drawing Sheets

(51) Int. Cl.
*A61B 5/00* (2006.01)
*A61B 5/026* (2006.01)
*A61B 5/055* (2006.01)
*G01R 33/54* (2006.01)

(52) U.S. Cl.
CPC .......... *A61B 5/055* (2013.01); *G01R 33/4838* (2013.01); *G01R 33/543* (2013.01); *G01R 33/5635* (2013.01)

(56) References Cited

U.S. PATENT DOCUMENTS

| | | | |
|---|---|---|---|
| 2009/0149733 A1 | 6/2009 | Guenther | |
| 2010/0274117 A1 | 10/2010 | Gunther et al. | |
| 2011/0181283 A1 | 7/2011 | Grinstead | |
| 2012/0139537 A1* | 6/2012 | Holland | G01R 33/4806 324/309 |
| 2012/0271157 A1* | 10/2012 | Wong | A61B 5/0042 600/419 |
| 2013/0085379 A1 | 4/2013 | Feinberg | |
| 2013/0123611 A1* | 5/2013 | Riederer | A61B 5/0263 600/419 |
| 2016/0018501 A1* | 1/2016 | Kimura | G01R 33/56308 324/322 |

OTHER PUBLICATIONS

Ye et al., "Correction for Vascular Artifacts in Cerebral Blood Flow Values Measured by Using Arterial Spin Tagging Techniques", MRM, vol. 37, pp. 226-235, 1997. (Year: 1997).*

Iryo et al., "Intracranial dural arteriovenous fistulas: evaluation with 3-T four-dimensional MR angiography using arterial spin labeling", Radiology, vol. 271, pp. 193-199, Published online Nov. 21, 2013. (Year: 2013).*

Feinberg et al., "Arterial Spin Labeling with Simultaneous Multi-Slice Echo Planar Imaging", Magnetic Resonance in Medicine, vol. 70, pp. 1500-1506, 2013. (Year: 2013).*

Matthias Günther et al: "Arterial Spin Labeling in Combination With a Look-Locker Sampling Strategy: Inflow Turbo-Sampling EPI-FAIR (ITS-FAIR)", Magnetic Resonance in Medicine, vol. 46, Jan. 1, 2001 (Jan. 1, 2001), pp. 974-984.

Teeuwisse WM et al: "Comparison of spin dynamics in pseudo-continuous and velocity-selective arterial spin labeling with and without vascular crushing", Proceedings of the International Society for Magnetic Resonance in Medicine, ISMRM, 19th Annual Meeting and Exhibition, Montreal, Quebec, May 7-13, 2011,Apr. 23, 2011 (Apr. 23, 2011), p. 2115.

Ye Frank: "Improving the ASL experiment with vascular crushing and background suppression", Proceedings of the International Society for Magnetic Resonance in Medicine, ISMRM, 20th Annual Meeting and Exhibition, Melbourne, Australia, May 5-11, 2012, Apr. 21, 2012.

Katherine L. Wright et al: "Simultaneous magnetic resonance angiography and perfusion (MRAP) measurement: Initial application in lower extremity skeletal muscle",JOURNAL of Magnetic Resonance Imaging, vol. 38, No. 5,Feb. 6, 2013 (Feb. 6, 2013), pp. 1237-1244.

* cited by examiner

MRI INVOLVING THE ACQUISITION OF AN ANGIOGRAPHY WEIGHTED IMAGE AND OF A PERFUSION WEIGHTED IMAGE

CROSS REFERENCE TO RELATED APPLICATIONS

This application is a U.S. national phase application of International Application No. PCT/EP2015/058359, filed on Apr. 17, 2015, which claims the benefit of EP Application Serial No. 14165302.2 filed on Apr. 18, 2014 and is incorporated herein by reference.

FIELD OF THE INVENTION

The invention relates to the field of magnetic resonance imaging in arterial spin labeling.

BACKGROUND OF THE INVENTION

Magnetic resonance (MR) imaging has shown the ability to provide information on cerebral hemodynamics in a noninvasive manner. With the availability of this information via MR imaging, MR imaging has proven a very valuable tool to enable the diagnosis of a variety of diseases. For example, perfusion imaging allows accessing the blood flow of an organ, e.g. the brain, in a complete non-invasive way which can be important information in patients with an altered vasculature. Originally, contrast agents were used to monitor the blood flow.

Recently, arterial spin labeling (ASL) was introduced, which avoids use of such contrast agent by using magnetic tagging of inflowing blood spins. MR imaging using ASL is capable of providing quantitative estimation of hemodynamic parameters such as cerebral blood flow, which were formerly only available using contrast agents. ASL typically comprises two phases, one with active arterial spin labeling and one control phase, which does not apply labeling. In the phase with arterial spin labeling, blood water spins flowing into a region of interest are marked by radio frequency (RF) pulses, e.g. magnetization of arterial water is inverted in proximity to the region of interest. After an inflow time required for the marked blood to travel into the region of interest, an image of this region is acquired. The acquired signal is modulated by the labeled blood that has flown into the tissue. In the control phase, the inflowing blood water spins remain un-inverted before the image is acquired, i.e. labeling is not performed. Despite the absence of labeling information, the modules of the control phase are performed in accordance with the above describes labeling and readout modules to acquire MR control information without labeling information. The data sets of both phases are subtracted to cancel out signal of stationary tissue and only yield signal of the inflown blood. The acquired images are hence sensitized to the magnetic difference between labeled spins and static tissue. Typically, phases with active arterial spin labeling and control phases interleave each other.

Another typical application of ASL is generation of angiography weighted images. Angiography refers to imaging the morphology of vessels or in cased of 4D- or time-resolved angiography to dynamically imaging the blood flow through the vessel.

In general, ASL is used as a sequence of a single preparation module, which can be either a labeling module or a control module as stated above, and a single type of readout module. There are several techniques used in the preparation module to achieve the effective labeling, also referred to as tagging, of the blood as well as the control condition, which rely on the utilization of arterial blood water spins as an endogenous tracer.

In general, ASL can be divided into different types depending on the strategy on how the blood spins are labeled and with individual merits and drawbacks. One type of ASL, so called pseudo-continuous or pulsed-continuous ASL (pCASL), employs a train of short and discrete RF pulses of about 0.5 ms length in conjunction with a synchronously pulsed gradient field during the labeling module. This RF pulse/gradient pattern is applied for durations of up to a few seconds and creates a thin inversion plane proximal to the imaging slices. All blood spins flowing through this labeling plane are being inverted due to a process called flow-driven adiabatic inversion. Similarly, the control condition is achieved by a very similar train of short and discrete RF pulses of about 0.5 ms length in conjunction with a synchronously pulsed gradient field during the labeling module, while not affecting the magnetization. Time-resolved information can be obtained by temporally encoding the preparation module or by repeating a similar readout module multiple times.

After application of the preparation module, tuning of the readout module can result in images with different contrasts, i.e. an angiographic image based on pCASL can be obtained by employing a short delay time between labeling and acquisition so that the labeled spins still remain inside the vessels. In contrast, for perfusion-weighted images, a long labeling bolus of up to a few seconds is employed with an increased delay time between labeling and image acquisition so that the magnetically labeled spins can travel to the region of interest thereby residing in the microvasculature and partly or completely exchange with tissue water molecules, thereby, reducing the overall detected or measured magnetization. The recorded signals are a sum of all different compartments in a pixel (voxel), i.e. a sum of tissue and microvascular magnetization, and possibly other compartments, such as cerebrospinal fluid (CSF). Application of crusher gradients in the readout can suppress intravascular signal, whereas subtraction of an ASL image with crusher gradients from an ASL image without crusher gradients enables the measurement of vascular signals, e.g. arterial blood volume, or the arterial inflow curves of the labeled blood.

In general, ASL is used as a combination of a single preparation module and a single type of acquisition, i.e. readout module. The choice and type of the respective modules depends on the information to be gathered from the final images, e.g. low or high spatial resolution depending on whether the images should present perfusion-weighted contrast or angiographic vessel morphology. Such multiple information can only be measured in separate image acquisitions which will prolong the overall scan time significantly. However, in general, fast data collection is required with respect to efficient workflow and therapy decision. For instance, in case of an acute stroke, imaging has to be performed as fast as possible to reduce the time to treatment to a minimum.

SUMMARY OF THE INVENTION

It is an object of the invention to provide a method for magnetic resonance imaging in arterial spin labeling, a MR imaging system for performing the above method, and a software package for upgrading a MR imaging system to perform the above method, which enable efficient use of arterial spin labeling in magnetic resonance imaging, which enable improved workflow in clinical routine practice, which provide reduced scan times, and which provide an increased level of relevant hemodynamic information in a short time.

This object is achieved by a method for magnetic resonance (MR) imaging of a subject of interest using arterial spin labeling, comprising the steps of performing a labeling module by applying magnetic and/or radio frequency (RF) fields to the subject of interest for labeling arterial blood in at least a labeling region thereof, performing a first readout module to obtain first MR information of the subject of interest in a region of interest using first parameters, performing a second readout module to obtain second MR information of the subject of interest in the region of interest using second parameters, and performing MR image generation of the region of interest based on the first and second MR information, wherein the first and second parameters of the first and second readout module are chosen to be different parameters.

The object is also achieved by a MR imaging system for providing an image representation of region of interest of a subject of interest positioned in an examination space of the MR imaging system, wherein the MR imaging system is adapted to perform the above method for MR imaging using arterial spin labeling.

The object is further achieved by a software package for upgrading a MR imaging system, whereby the software package contains instructions for controlling the MR imaging system according to the above method for MR imaging using arterial spin labeling.

According to the invention, at least two readout modules are combined after a single labeling module. The total encoded magnetization due to the labeling pulse is partly used for the first readout and partly for the second readout. Hence, different contrasts can be provided after a single labeling module, thereby acquiring multi-modal hemodynamic information almost at the same moment in time and in a single scan. The need for separate acquisitions can be overcome when monitoring hemodynamic changes, for example during a functional task or a hemodynamic challenge. Scan-times can be reduced when two types of information are needed, for which readouts with different parameters are required. The combination of e.g. two readout modules in combination with a single labeling module can reduce scan time to almost a 50% compared to performing both readout modules individually after a labeling module each. This improves the workflow in clinical routine practice and enables important improvements in time-critical diagnostics based on MR imaging, e.g. for application in acute stroke patients.

Based on the different parameters of the first and second readout module, different scanning contrasts can be provided using a single labeling module. This enables acquisition of multi-modal hemodynamic information at almost the same moment in time in a single scan. A decrease in the acquisition time can be achieved by employing only one labeling module for two types of acquisition, whereby the first readout module leaves enough encoded magnetization as well as time to acquire relevant information for e.g. the second scanning contrast. This refers to a location of the labeled blood, e.g. whether the labeled blood is supposed to be present in the relevant region of interest during the second readout module, and time constraints of the labeling itself, e.g. if the blood still has a sufficiently strong label for acquisition during the second readout module.

The first and second parameters of the first and second readout module can comprise parameters like excitation pulse, echo time, k-space filling strategy, number of acquired k-space lines per labeling module, readout pulse, pulse type, pulse angle, flip angle, and others. The first and second parameters of the first and second readout module can differ in at least one parameter, multiple parameters, or even all parameters, depending on the kind of information to be obtained when performing the first and second readout, respectively.

MR image generation of the region of interest based on the first and second MR information refers to the generation of at least one two- or three-dimensional image. Typically, a 3D scan is generated based on the first and second MR information. Furthermore, the method can be performed to generate one or multiple images/3D scans.

Performing a labeling module is generally known to a person skilled in the Art, so that no further details need to be given.

According to a preferred embodiment the method comprises performing repeatedly the steps of performing a labeling module and performing a first and second readout module. The sequence of these steps has to be maintained, so that the first and second readout module can provide the first and second MR information. In the step of performing MR image generation of the region of interest based on the first and second MR information, the first and second MR information from all or multiple of the repeated readouts can be used for generating the MR image. Accordingly, the repetitions can be stopped when sufficient k-space samples have been acquired to obtain a desired resolution for the MR image. Hence, k-space samples can be acquired in different segments and be combined to provide the MR image as desired. In an alternative embodiment, the method is continuously performed to enable instantaneous imaging. In a further alternative embodiment, the first or second readout is repeatedly performed to fill k-space, and the other, i.e. the second or the first readout, respectively, is continuously performed for instantaneous imaging. Accordingly, the continuously performed readout will be repeated according to the repetitions of the first or second readout and can subsequently be averaged.

According to a preferred embodiment the method comprises the additional steps of performing a control module, and performing at least a first readout module to obtain first MR control information of the subject of interest in a region of interest using first parameters or a second readout module to obtain second MR control information of the subject of interest in a region of interest using second parameters. The control module refers to a module prior to the at least first or second readout module, which is performed to operate the MR imaging system as much as possible in a similar way as when performing the labeling module but without labeling the blood, so that differences between the acquired MR control information and the MR information acquired after the labeling module are best case limited to the influence of the labeled blood. Nevertheless, the control module could theoretically also be a void module, where the MR imaging system is not operated, or a module, where only parts of the operation of the labeling module are performed. The control information can be used e.g. to acquire perfusion information, when an image with ASL labeling is acquired and compared to an image with the control condition of ASL, i.e. the control image. E.g. subtraction of images acquired with labeling and the control images provides a perfusion-weighted image. Hence, in the step of performing MR image generation of the region of interest based on the first and second MR information, also the at least first or second MR control information can be used for generating the MR image. Depending on the first and second parameters, the control image can be used for the first readout and the second readout, or for just one of them.

According to a preferred embodiment the steps of performing a labeling module and performing a first and second readout module are performed interleaved with the steps of performing a control module and performing at least a first readout module or a second readout module. Hence, MR information acquired after a labeling module and MR control information can be obtained e.g. alternately, further limiting the impact as much as possible to the labeled blood. The interleaved performance of the labeling module and the control module with the respective subsequent readouts in general refer to alternately performing the labeling module and the control module. Nevertheless, also other sequences of labeling modules and control modules with the respective subsequent readouts can be performed. In the step of performing MR image generation of the region of interest, the first and second MR information from all or multiple of the repeated readouts can be used together with the first and second MR control information from all or multiple of the repeated readouts for generating the MR image. Accordingly, the repetitions can be stopped when sufficient k-space samples have been acquired to obtain a desired resolution for the MR image. Hence, k-space samples can be acquired in different segments and be combined to provide the MR image as desired. In an alternative embodiment, the method is continuously performed to enable instantaneous imaging. In a further alternative embodiment, the first or second readout is repeatedly performed to fill k-space, and the other, i.e. the second or the first readout, respectively, is continuously performed for instantaneous imaging. Accordingly, the continuously performed readout will be repeated according to the repetitions of the first or second readout and can subsequently be averaged.

According to a preferred embodiment the step of performing a labeling module comprises employing a pseudo-continuous or pulsed-continuous ASL. Pseudo-continuous or pulsed-continuous ASL (pCASL), employs a train of short and discrete RF pulses of about 0.5 ms length in conjunction with a synchronously pulsed gradient field. This RF pulse/gradient pattern is applied for durations of up to a few seconds and creates a thin inversion plane proximal to the imaging slices. All blood spins flowing through this labeling plane are being inverted due to a process called flow-driven adiabatic inversion. Therefore, time-resolved information can be obtained by temporally encoding the labeling module.

According to a preferred embodiment the step of performing a labeling module comprises employing a temporally encoded labeling train, e.g. a Hadamard encoded labeling train. The Hadamard encoded labeling train refers to a labeling module that interleaves label and control sub-modules, which enables distinction between blood magnetization states. Therefore, the use of the Hadamard encoded labeling train allows the acquisition of time series in a very efficient way since all measured data sets are used for reconstruction of each single time step. In particular, the Hadamard encoded labeling train provides a series of sub-modules, that can perform labeling of the arterial blood, and sub-modules for control, which do not label the blood. Over the different repetitions, the order of the sub-modules can vary, so that by clever adding and subtraction of measurements, effectively a control minus label condition can be performed. Using the temporally encoded labeling trains enables the combination of a labeling and control phase, so that readouts after a labeling module employing temporally encoded labeling trains overcomes the need for application of separate control modules.

According to a preferred embodiment the method comprises choosing the labeling region and the region of interest as different regions. The labeling region and the region of interest can be disjunctive regions or partially overlapping regions. Hence, the blood can be labeled in the most suitable region, e.g. in the arteries of the neck when the region of interest refers to the brain of the subject of interest. Nevertheless, the brain itself is as region of interest mostly relevant for the MR scan, so that the readout modules cover the brain to provide MR information thereof. In alternative embodiments, the labeling module and the readout modules can be performed in the same region, i.e. the region of interest and the labeling region are identical, or the region of interest comprises the labeling region or the labeling region comprises the region of interest.

According to a preferred embodiment the step of performing a first readout module comprises using first parameters for angiography weighted images. Angiography refers to imaging the morphology of vessels or in case of 4D- or time-resolved angiography to dynamically imaging the blood flow through the vessel. Angiography imaging that can be decoded for inflow time measurements, which can leave enough signal for a subsequent second readout, e.g. a perfusion-weighted readout.

According to a preferred embodiment the step of performing a second readout module comprises using second parameters for perfusion weighted images. Perfusion information refers to the spatial distribution of blood flow in e.g. an organ. Hence, perfusion information is valuable to determine if blood flow of an organ, e.g. the brain, is sufficient or not at a specific location in the organ or in the organ as a whole. For perfusion-weighted images, a long labeling bolus of up to a few seconds is employed with an increased delay time between labeling and image acquisition so that the labeled arterial blood can travel to the region of interest and exchange with tissue water molecules, thereby, reducing the overall tissue magnetization.

According to a preferred embodiment the step of performing a first readout module or a second readout module comprises using first or second parameters, respectively, for acquiring non vascular crushed image data. Application of crusher gradients in the readout module can suppress intravascular signals, whereas subtraction of an ASL image with crusher gradients from an ASL image without crusher gradients enables the measurement of vascular signals, e.g. arterial blood volume, or arterial inflow curves of the labeled blood. By way of example, if the parameters refer to the first parameters, the parameters can be set to acquiring non vascular crushed image data after a 45° excitation pulse, if the parameters refer to the second parameters, the parameters can be set to acquiring non vascular crushed image data after a 90° excitation pulse.

According to a preferred embodiment the step of performing a first readout module or a second readout module comprises using first or second parameters, respectively, for acquiring vascular crushed image data. Application of crusher gradients in the readout module can suppress intravascular signals, whereas subtraction of an ASL image with crusher gradients from an ASL image without crusher gradients enables the measurement of vascular signals, e.g. arterial blood volume, or arterial inflow curves of the labeled blood. By way of example, if the parameters refer to the first parameters, the parameters can be set to acquiring non vascular crushed image data after a 45° excitation pulse, if the parameters refer to the second parameters, the parameters can be set to acquiring non vascular crushed image data after a 90° excitation pulse.

According to a preferred embodiment the method comprises performing a third readout module subsequent to the second readout module to obtain third MR information of the subject of interest based on the labeled blood, wherein the third readout module is performed with different parameters compared to the first and second readout module. Hence, still further information of the subject of interest can be acquired in one sequence having a single labeling module. This enables a further increase in efficiency when performing MR imaging methods. Accordingly, the step of performing MR image generation of a region of interest can be performed based on the first, second and third MR information. In principle, even higher numbers of readout modules can be performed after a single labeling module, so that still further MR information can be acquired and used for MR image generation. The number of readout modules is merely limited by the available time for readouts after the labeling module. The principles discussed above in respect to performing the first and second readout module also apply to the third readout module, and to any further readout module.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
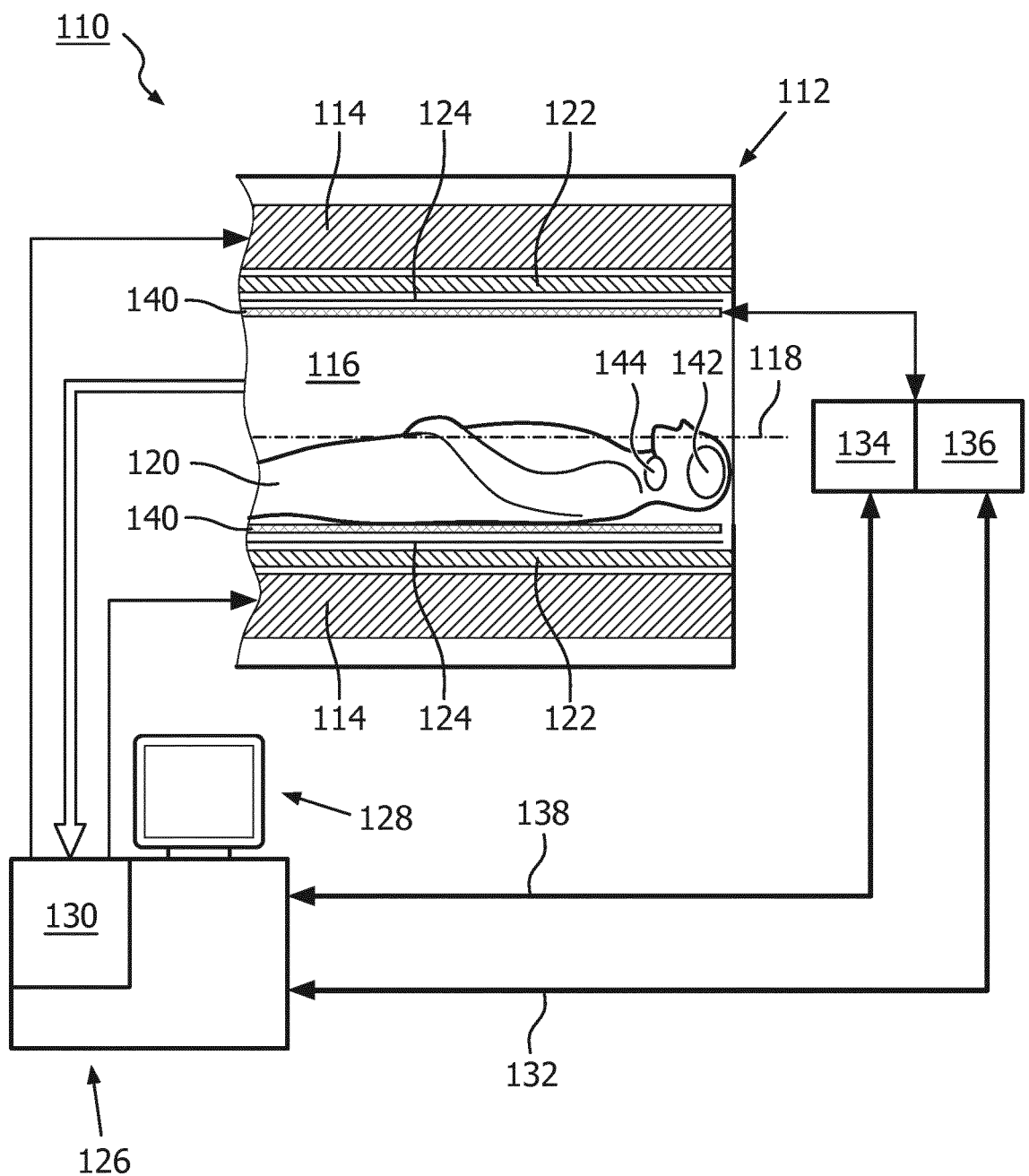
FIG. 1 is a schematic illustration of a part of a magnetic resonance (MR) imaging system in accordance with the invention.

FIG. 1 shows a schematic illustration of an embodiment of a magnetic resonance (MR) imaging system 110 in accordance with the invention. The MR imaging system 110 can be a MR imaging system known in the Art, which is operated as described later in detail to perform MR imaging using arterial spin labeling.

The MR imaging system 110 comprises an MR scanner 112. The MR imaging system 110 further includes a main magnet 114 provided for generating a static magnetic field. The main magnet 114 has a central bore that provides an examination space 116 around a center axis 118 for a subject of interest 120, usually a patient, to be positioned within. In this embodiment, the central bore and therefore the static magnetic field of the main magnet 114 has a horizontal orientation in accordance with the center axis 118. In an alternative embodiment, the orientation of the main magnet 114 can be different, e.g. to provide the static magnetic field with a vertical orientation. Further, the MR imaging system 110 comprises a magnetic gradient coil system 122 provided for generating gradient magnetic fields superimposed to the static magnetic field. The magnetic gradient coil system 122 is concentrically arranged within the bore of the main magnet 114, as known in the art.

Further, the MR imaging system 110 includes a radio frequency (RF) antenna device 140 designed as a whole-body coil having a tubular body. The RF antenna device 140 is provided for applying an RF magnetic field to the examination space 116 during RF transmit phases to excite nuclei of the subject of interest 120, in particular in a region of interest 142, which shall be covered by MR images. The RF antenna device 140 is also provided to receive MR signals from the excited nuclei during RF receive phases. In a state of operation of the MR imaging system 110, RF transmit phases and RF receive phases are taking place in a consecutive manner. The RF antenna device 140 is arranged concentrically within the bore of the main magnet 114. As is known in the art, a cylindrical metal RF screen 124 is arranged concentrically between the magnetic gradient coil system 122 and the RF antenna device 140.

Moreover, the MR imaging system 110 comprises an MR image reconstruction unit 130 provided for reconstructing MR images from the acquired MR signals and an MR imaging system control unit 126 with a monitor unit 128 provided to control functions of the MR scanner 112, as is commonly known in the art. Control lines 132 are installed between the MR imaging system control unit 126 and an RF transmitter unit 134 that is provided to feed RF power of an MR radio frequency to the RF antenna device 140 via an RF switching unit 136 during the RF transmit phases. The RF switching unit 136 in turn is also controlled by the MR imaging system control unit 126, and another control line 138 is installed between the MR imaging system control unit 126 and the RF switching unit 136 to serve that purpose. During RF receive phase, the RF switching unit 136 directs the MR signals from the RF antenna device 140 to the MR image reconstruction unit 130 after pre-amplification.

Figure 2:
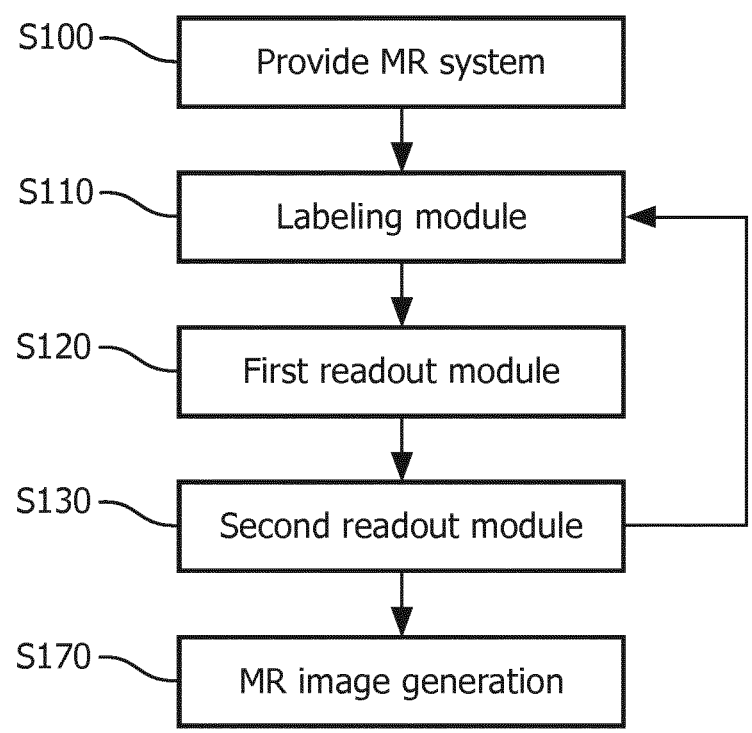
FIG. 2 is a flow chart indicating a generic method for magnetic resonance (MR) imaging using arterial spin labeling according to a first embodiment.

FIG. 2 indicates a generic method for magnetic resonance (MR) using arterial spin labeling imaging according to a first embodiment.

In step S100 the above MR imaging system 110 is provided. Furthermore, the subject of interest 120 is located in the examination space 116.

In step S110 a labeling module 200 is performed using the MR imaging system 110 applying magnetic and/or radio frequency (RF) fields to the subject of interest 120 for labeling arterial blood in a labeling region 144. The labeling region 144 in this embodiment refers to a neck region of the subject of interest 120. Accordingly, blood flowing through the arteries of the neck is labeled during the labeling module 200. The labeling module 200 can also be seen with respect to FIG. 4, where three different embodiments of the method are depicted.

In step S120 a first readout module 202 is performed to obtain first MR information of the subject of interest 120 based on the labeled blood using first parameters.

In step S130 a second readout module 204 is performed to obtain second MR information of the subject of interest 120 based on the labeled blood using second parameters.

Figure 4:
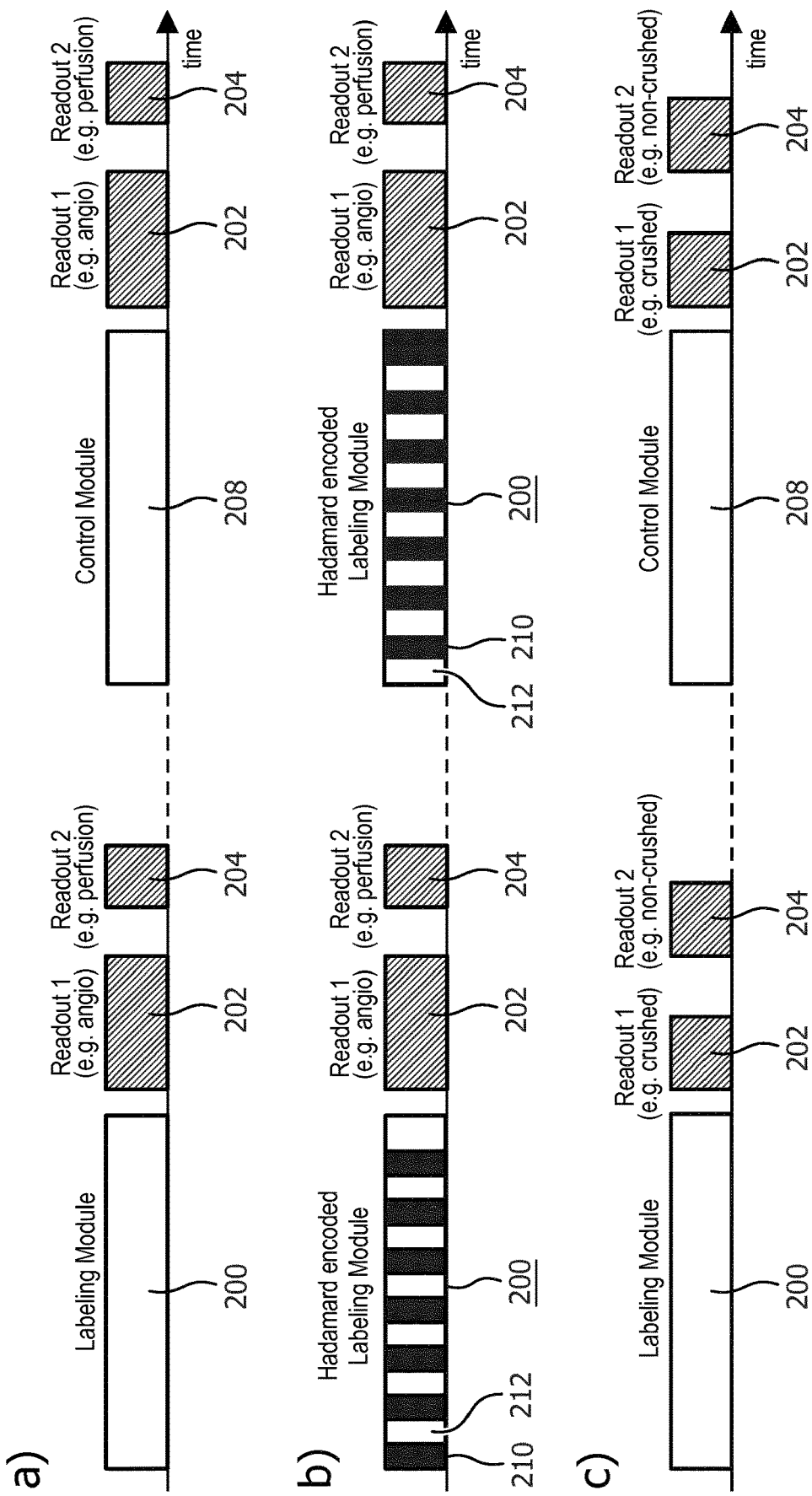
Figure 5:
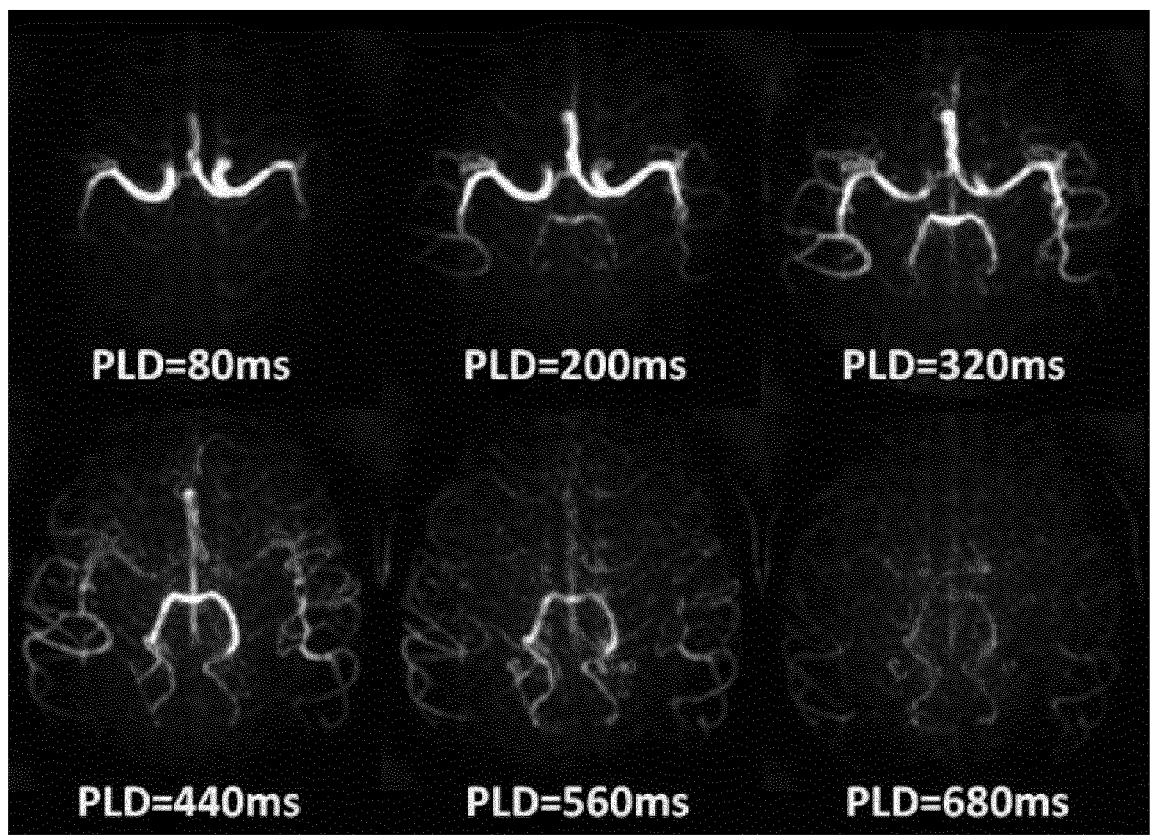
Figure 6:
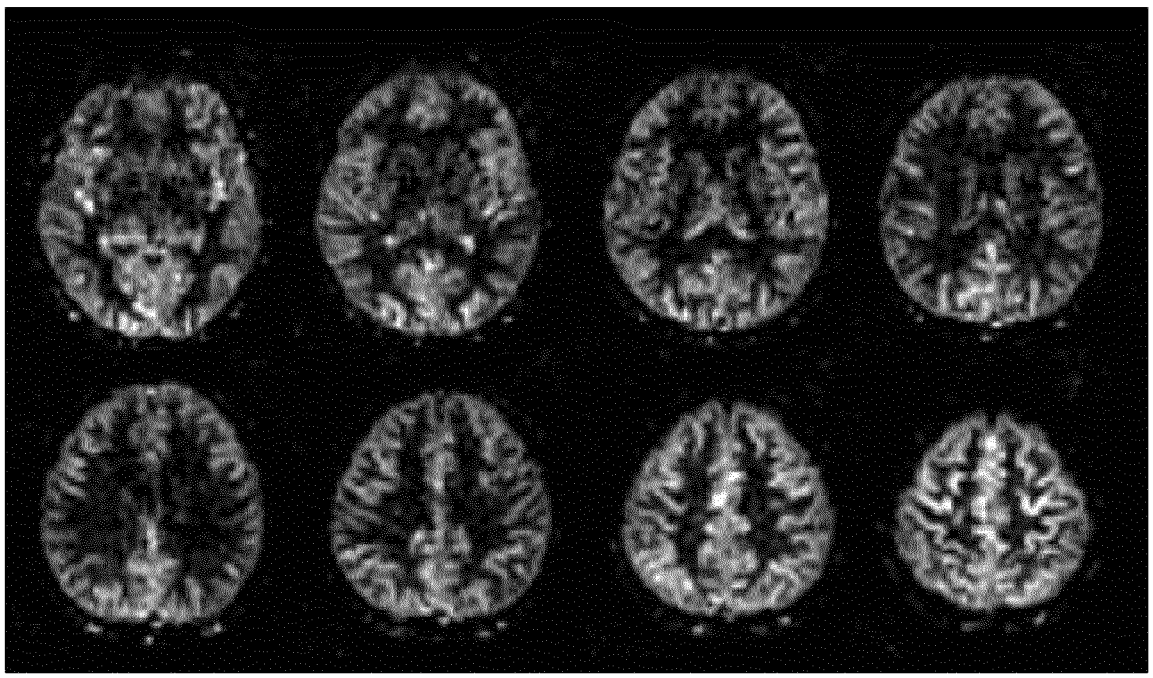

The first and second parameters of the first and second readout module 202, 204 are chosen to be different parameters, as can be seen in detail in respect to the embodiments depicted in FIG. 4. Based on the different parameters of the first and second readout module, different scanning contrasts can be provided using a single labeling module.

As can be seen in FIG. 2, the modules 200, 202, 204 are performed repeatedly, i.e. steps S110, S120, and S130 are repeated in this order until sufficient k-space samples have been achieved to obtain sufficient information for a desired MR image.

In step S170 MR image generation of the region of interest 142 based on the first and second MR information is performed. Hence, k-space samples acquired in the repeated first and second readout modules 202, 204 are combined to provide the MR image of the region of interest 142. The MR image of the region of interest 142 is provided as a 3D scan. The region of interest 142 in this embodiment is the brain of the subject of interest 120.

Figure 3:
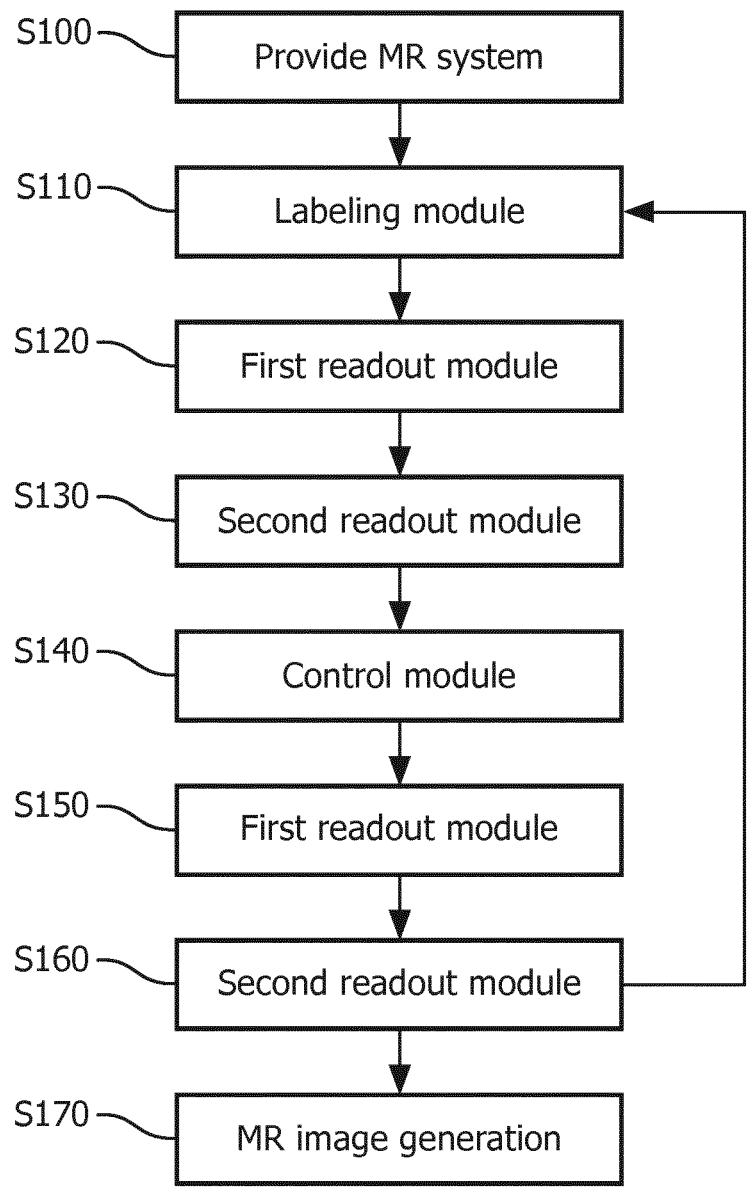
FIG. 3 is a flow chart indicating a generic method for magnetic resonance (MR) imaging using arterial spin labeling according to a first embodiment, FIG. 4 contains three timing diagrams of three methods as generically shown in FIG. 3 in accordance with the third, fourth and fifth embodiment of the present invention, FIG. 5 contains an illustration of time-resolved angiography weighted images based on a first readout, and FIG. 6 contains an illustration of perfusion weighted images based on a second readout.

FIG. 3 indicates a generic method for magnetic resonance (MR) using arterial spin labeling imaging according to a second embodiment. Method steps, which do not differ from those of the first embodiment, are assigned the same step number. Reference is made to the respective description of these method steps.

In step S100 the above MR imaging system 110 is provided. Furthermore, the subject of interest 120 is located in the examination space 116.

In step S110 a labeling module 200 is performed using the MR imaging system 110 applying magnetic and/or radio frequency (RF) fields to the subject of interest 120 for labeling arterial blood in a labeling region 144. The labeling region 144 in this embodiment refers to a neck region of the subject of interest 120. Accordingly, blood flowing through the arteries of the neck is labeled during the labeling module 200. The labeling module 200 can also be seen with respect to FIG. 4, where three different embodiments of the method are depicted.

In step S120 a first readout module 202 is performed to obtain first MR information of the subject of interest 120 based on the labeled blood using first parameters.

In step S130 a second readout module 204 is performed to obtain second MR information of the subject of interest 120 based on the labeled blood using second parameters.

The first and second parameters of the first and second readout module 202, 204 are chosen to be different parameters, as can be seen in detail in respect to the embodiments depicted in FIG. 4. Based on the different parameters of the first and second readout module, different scanning contrasts can be provided using a single labeling module 200.

In step S140 a control module 208 is performed using the MR imaging system 110. The control module 208 refers to a module, which is performed to operate the MR imaging system 110 as much as possible in a similar way as when performing the labeling module 200, but without labeling the blood in the labeling region 144. Accordingly, differences between the acquired MR control information and the acquired MR information are best case limited to the influence of the labeled blood.

In step S150 a first readout module 202 is performed to obtain first MR control information of the subject of interest 120 using the first parameters. The first parameters of the first readout module 202 in steps S120 and S150 are chosen identical.

In step S160 a second readout module 204 is performed to obtain second MR control information of the subject of interest 120 using the second parameters. The second parameters of the second readout module 202 in steps S130 and S160 are chosen identical.

As can be seen in FIG. 3, the modules 200, 202, 204, 208 are performed repeatedly in the sequence as described above, i.e. steps S110, S120, S130, S140, S150, and S160 are repeated in this order until sufficient k-space samples have been achieved to obtain sufficient MR information and MR control information for a desired MR image.

In step S170 MR image generation of a region of interest 142 based on the first and second MR information as well as the first and second MR control information is performed. Hence, k-space samples acquired in the repeated first and second readout modules 202, 204 are combined to provide the MR image of the region of interest 142. The MR image of the region of interest 142 is provided as a 3D scan. The region of interest 142 in this embodiment is the brain of the subject of interest 120. Based on the MR control information perfusion information is provided by subtraction of MR images acquired with labeling module 200 and control images acquired with control module 208 to provide a perfusion-weighted image. Hence, in the step of performing MR image generation of the region of interest 142 is based on the first and second MR information as well as the at first and second MR control information.

A further method corresponding to a third embodiment will now be described with reference to FIG. 4a, i.e. the upper diagram of FIG. 4. The method is based on the method according to the second embodiment shown in FIG. 3, so that details are only provided where required.

According to the method of the third embodiment, in step S110 the labeling module 200 is performed employing a pseudo-continuous or pulsed-continuous ASL. Pseudo-continuous or pulsed-continuous ASL (pCASL), employs a train of short and discrete RF pulses of about 0.5 ms length in conjunction with a synchronously pulsed gradient field. This RF pulse/gradient pattern is applied for durations of up to a few seconds and creates a thin inversion plane proximal to the imaging slices. All blood spins flowing through this labeling plane are being inverted due to a process called flow-driven adiabatic inversion. Still further, according to the method of the third embodiment, the first readout module 202 in step S120 comprises using first parameters for angiography weighted images. Angiography refers to imaging the morphology of vessels or in case of 4D- or time-resolved angiography to dynamically imaging the blood flow through the vessel. Angiography imaging can be decoded for inflow time measurements, which can leave enough signal for a subsequent second readout module 204, e.g. a perfusion-weighted readout. As first parameters, the first readout module 202 is set to perform a series of small flip angle turbo-field echo (TFE) pulses, e.g. 30 times 7° flip angle, area set as readout part of an angiography 3D-volume.

The second readout module 204 comprises using second parameters for perfusion weighted images. Perfusion imaging allows accessing the blood flow of an organ, e.g. the brain, in a complete non-invasive way which can be important information in patients with an altered vasculature. Perfusion information refers to the spatial distribution of blood flow in e.g. an organ. Hence, perfusion information is valuable to determine if blood flow of an organ is sufficient or not at a specific location in the organ or in the organ as a whole. For perfusion-weighted images, a long labeling bolus of up to a few seconds is employed with respect to the labeling module 200 with an increased delay time between labeling and image acquisition so that the labeled arterial blood can travel to the region of interest 142 and exchange with tissue water molecules, thereby, reducing the overall tissue magnetization. As second parameters, the second readout module 204 is set to perform a 90° multislice EPI readout to acquire perfusion weighted images.

In step S140 a control module 208 is performed using the MR imaging system 110, wherein the MR imaging system 110 is operated as much as possible in a similar way as when performing the labeling module 200, but without labeling the blood in the labeling region 144.

In step S150 a first readout module 202 is performed to obtain first MR control information of the subject of interest 120 using the first parameters. The first parameters of the first readout module 202 in steps S120 and S150 are chosen identical.

In step S160 a second readout module 204 is performed to obtain second MR control information of the subject of interest 120 using the second parameters. The second parameters of the second readout module 202 in steps S130 and S160 are chosen identical.

In step S170, the MR image is generated as a 3D scan in this embodiment containing angiography and perfusion information. In respect to the perfusion information, image data based on the second readout 204 with the prior labeling module 200 and image data based on the second readout 204 with the prior control module 208 are compared. In particular, the image acquired with the prior labeling module 200 is subtracted from the image acquired with the prior control module 208. In an alternative embodiment, a 2D scan is generated.

A further method corresponding to a fourth embodiment will now be described with reference to FIG. 4b, i.e. the middle diagram of FIG. 4. The method is based on the method according to the first embodiment shown in FIG. 3, so that details are only provided where required. Additionally, the method according to the fourth embodiment is identical to that of the third embodiment in respect to the readout modules 202, 204, i.e. steps S120 and S130. Furthermore, also the step S170 of generating the MR image is identical. Accordingly, differences only exist in respect to the labeling module 200, i.e. step S110, as described below.

According to the method of the fourth embodiment, in step S110 the labeling module 200 is performed employing a temporally encoded labeling train, which is a Hadamard encoded labeling train in this embodiment. The Hadamard encoded labeling train refers to a labeling module 200 that interleaves labeling and control sub-modules 210, 212, which enables distinction between blood magnetization states. Accordingly, the Hadamard encoded labeling train provides a series of sub-modules 210, that can perform labeling of the arterial blood, and sub-modules 212 for control, which do not label the blood. Hence, first and second MR control information are obtained with the same readout modules 202, 204, which are subsequently performed to acquire the first and second MR information. As can be seen in FIG. 4, middle diagram, the order of the sub-modules 210, 212 varies over the different repetitions of the labeling module 200.

A more detailed method corresponding to a fifth embodiment will now be described with reference to FIG. 4c, i.e. the lower diagram of FIG. 4. The method is based on the method shown in FIG. 3, so that details are only provided where required. Additionally, the method according to the fifth embodiment is identical to that of the third embodiment in respect to the labeling module 200 and the control module S208 in steps S110 and S140.

According to the method of the fifth embodiment, in step S110 the labeling module 200 is performed employing a pseudo-continuous or pulsed-continuous ASL.

In step S120, a first readout module 202 is performed using first parameters. As first parameters, the first readout module 202 is set to perform a readout for acquiring first non vascular crushed image data after a 45° excitation pulse.

In step S130, a second readout module 204 is performed using second parameters. As second parameters, the second readout module 204 is set to perform a readout for acquiring vascular crushed image data after a 90° readout pulse.

In step S140 a control module 208 is performed using the MR imaging system 110, wherein the MR imaging system 110 is operated as much as possible in a similar way as when performing the labeling module 200, but without labeling the blood in the labeling region 144.

In step S150 a first readout module 202 is performed to obtain first MR control information of the subject of interest 120 using the first parameters. The first parameters of the first readout module 202 in steps S120 and S150 are chosen identical.

In step S160 a second readout module 204 is performed to obtain second MR control information of the subject of interest 120 using the second parameters. The second parameters of the second readout module 202 in steps S130 and S160 are chosen identical.

In step S170, the MR image is generated as a 3D scan in this embodiment.

In one embodiment, a computer-readable medium such as a storage device, a floppy disk, compact disc, CD, digital versatile disc, DVD, Blu-ray disc, or a random access memory, RAM, is provided that contains a set of instructions that causes the control unit 126 of the MR imaging system 110 to perform the above method.

Accordingly, a computer program product comprising a computer-usable medium including computer-usable program code is provided, wherein the computer-usable program code is adapted to execute the above method.

In a further embodiment a software package is provided for upgrading a MR imaging system 110, whereby the software package contains instructions for controlling the MR imaging system 110 to perform the above method.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 110 magnetic resonance (MR) imaging system
112 magnetic resonance (MR) scanner
114 main magnet
116 RF examination space
118 center axis
120 subject of interest
122 magnetic gradient coil system
124 RF screen
126 MR imaging system control unit
128 monitor unit
130 MR image reconstruction unit
132 control line
134 RF transmitter unit
136 RF switching unit
138 control line
140 radio frequency (RF) antenna device
142 region of interest
144 labeling region
200 labeling module
202 first readout module
204 second readout module
208 control module
210 sub-module for labeling
212 sub-module for control

The invention claimed is:

1. A method, comprising:
performing a blood labeling operation by applying magnetic and/or radio frequency fields to a subject of interest to label arterial blood in at least a labeling region thereof;
obtaining at a first time point, using first parameters, first magnetic resonance (MR) information related to vessel morphology of the subject of interest in a region of interest;
obtaining at a second time point which is subsequent to the first time point, using second parameters, second MR information related to blood perfusion in the subject of interest in the region of interest, wherein the first MR information related to vessel morphology obtained using the first parameters, and the second MR information related to blood perfusion obtained using the second parameters, are obtained based on the same labeled blood as each other, which was labeled by the blood labeling operation; and
performing MR image generation of the region of interest based on the first MR information and the second MR information including generation of at least one two-dimensional or three-dimensional image based on the first MR information and the second MR information, wherein the first parameters are chosen as parameters for angiography weighted images as to present vessel morphology and include performing a readout for acquiring non vascular crushed image data after a 45° excitation pulse, and wherein the second parameters are chosen as parameters for perfusion weighted images different from the first parameters and include performing a readout for acquiring vascular crushed image data after a 90° excitation pulse.

2. The method of claim 1, comprising
performing repeatedly the applying of the magnetic and/or radio frequency fields to the subject of interest for labeling the arterial blood, and the obtaining of the first MR information using the first parameters and obtaining the second MR information using the second parameters.

3. The method of claim 1, further comprising:
performing a control operation without labeling the arterial blood, and
at a third time point, subsequent to the control operation, obtaining first MR control information of the subject of interest in the region of interest using the first parameters, or obtaining second MR control information of the subject of interest in the region of interest using the second parameters.

4. The method of claim 3, wherein
the applying of the magnetic and/or radio frequency fields for labeling the arterial blood and the obtaining of the first and second MR information are interleaved with performing the control operation and obtaining at least one of the first MR control information and the second MR control information.

5. The method of claim 1, wherein applying the magnetic and/or radio frequency fields for labeling the arterial blood comprises employing a pseudo-continuous or pulsed-continuous arterial spin labeling.

6. The method of claim 1, wherein applying the magnetic and/or radio frequency fields for labeling the arterial blood comprises employing a temporally encoded labeling train.

7. The method of claim 6, wherein the temporally encoded labeling train is Hadamard encoded labeling train.

8. The method of claim 1, wherein the labeling region and the region of interest do not overlap each other.

9. The method of claim 1, further comprising obtaining third MR information of the subject of interest based on the same labeled arterial blood as was used to obtain the first MR information at the first time point and to obtain the second MR information at the second time point, subsequent to obtaining the second MR information, wherein the third MR information is obtained with different parameters compared to the first and second parameters.

10. The method of claim 1, wherein applying the magnetic and/or radio frequency fields to the subject of interest for labeling the arterial blood in at least the labeling region thereof comprises employing a train of short and discrete RF pulses of 0.5 ms length in conjunction with a synchronously pulsed gradient field, for a plurality of seconds.

11. The method of claim 1, wherein obtaining at the first time point the first MR information of the subject of interest in the region of interest includes performing a series of turbo-field echo (TFE) pulses with a 7° flip angle.

12. The method of claim 1, wherein obtaining at the second time point the second MR information of the subject of interest in the region of interest includes performing a 90° multislice EPI readout to acquire the perfusion weighted images.

13. A system, comprising:
a main magnet;
a gradient coil system;
a radio frequency antenna;
a magnetic resonance (MR) image reconstruction unit; and
an MR imaging system control unit,
wherein the MR imaging system control unit is configured to control the main magnet, gradient coil system, the radio frequency antenna, and the MR image reconstruction unit to:
apply magnetic and/or radio frequency fields to a subject of interest for labeling arterial blood in at least a labeling region thereof,
obtain at a first time point, using first parameters, first MR information related to vessel morphology of the subject of interest in a region of interest using first parameters,
obtain at a second time point which is subsequent to the first time point, using second parameters, second MR information related to blood perfusion in the subject of interest in the region of interest, wherein the first MR information related to vessel morphology obtained using the first parameters, and the second MR information related to blood perfusion obtained using the second parameters, are obtained based on the same labeled blood as each other, which was labeled by the blood labeling operation, and
perform MR image generation of the region of interest based on the first MR information and the second MR information including generation of at least one two-dimensional or three-dimensional image based on the first MR information and the second MR information,
wherein the first parameters are chosen as parameters for angiography weighted images as to present vessel morphology and include performing a readout for acquiring non vascular crushed image data after a 45° excitation pulse, and wherein the second parameters are chosen as parameters for perfusion weighted images different from the first parameters and include performing a readout for acquiring vascular crushed image data after a 90° excitation pulse.

14. The system of claim 13, wherein the MR imaging system control unit is configured to control the main magnet, gradient coil system, the radio frequency antenna, and the MR image reconstruction unit to perform repeatedly the applying of the magnetic and/or radio frequency fields to the subject of interest for labeling the arterial blood, and the obtaining of the first MR information using the first parameters and obtaining the second MR information using the second parameters.

15. The system of claim 13, wherein the MR imaging system control unit is further configured to control the main magnet, gradient coil system, the radio frequency antenna, and the MR image reconstruction unit to:
perform a control operation without labeling the arterial blood, and
at a third time point, subsequent to the control operation, obtain first MR control information of the subject of interest in the region of interest using the first parameters, or obtain second MR control information of the subject of interest in the region of interest using the second parameters.

16. The system of claim 15, wherein the applying of the magnetic and/or radio frequency fields for labeling the arterial blood and the obtaining of the first and second MR information are interleaved with performing the control operation and obtaining at least one of the first MR control information and the second MR control information.

17. The system of claim 13, wherein applying the magnetic and/or radio frequency fields for labeling the arterial blood comprises employing a pseudo-continuous or pulsed-continuous arterial spin labeling.

18. The system of claim 13, wherein applying the magnetic and/or radio frequency fields for labeling the arterial blood comprises employing a temporally encoded labeling train.

19. The system of claim 13, wherein the labeling region and the region of interest do not overlap each other.

20. The system of claim 13, wherein applying the magnetic and/or radio frequency fields to the subject of interest for labeling the arterial blood in at least the labeling region thereof comprises employing a train of short and discrete RF pulses of 0.5 ms length in conjunction with a synchronously pulsed gradient field, for a plurality of seconds.

\* \* \* \* \*